(12) United States Patent
Fukano et al.

(10) Patent No.: US 7,041,971 B2
(45) Date of Patent: May 9, 2006

(54) APPARATUS AND METHOD FOR DETECTING CHEMICAL AGENTS

(75) Inventors: Masumi Fukano, Yokohama (JP); Shigeru Honjo, Otsuki (JP); Hisashi Nagano, Hachioji (JP); Yasuaki Takada, Kiyose (JP); Yasuo Seto, Kashiwa (JP); Teruo Itoi, Otone (JP); Kazumitsu Iura, Fuchu (JP)

(73) Assignees: Hitachi, Ltd., Tokyo (JP); President of National Research of Police Science, Kashiwa (JP)

( * ) Notice: Subject to any disclaimer, the term of this patent is extended or adjusted under 35 U.S.C. 154(b) by 98 days.

(21) Appl. No.: 10/644,806

(22) Filed: Aug. 21, 2003

(65) Prior Publication Data

US 2005/0092915 A1 May 5, 2005

(30) Foreign Application Priority Data

Mar. 24, 2003 (JP) ........................ 2003-080380

(51) Int. Cl.
*H01J 49/10* (2006.01)

(52) U.S. Cl. .................. 250/288; 250/281; 250/282
(58) Field of Classification Search ............... 250/288, 250/282, 281, 309, 283
See application file for complete search history.

(56) References Cited

U.S. PATENT DOCUMENTS 4,551,624 A * 11/1985 Spangler et al. ............ 250/287

| 6,053,059 | A | | 4/2000 | Muranaka et al. |
| 6,188,065 | B1 | * | 2/2001 | Takada et al. ............... 250/288 |
| 6,326,615 | B1 | * | 12/2001 | Syage et al. ................. 250/287 |
| 6,649,910 | B1 | * | 11/2003 | Sakairi ........................ 250/288 |
| 2003/0015657 | A1 | | 1/2003 | Takada et al. |
| 2003/0020013 | A1 | * | 1/2003 | Sakairi ........................ 250/288 |
| 2004/0084614 | A1 | * | 5/2004 | Honjo et al. ................. 250/281 |

FOREIGN PATENT DOCUMENTS

DE  196 08 963 A1  10/1996
WO  WO 02/25265 A1  3/2002

* cited by examiner

Primary Examiner—Nikita Wells
Assistant Examiner—Johnnie L Smith, II
(74) Attorney, Agent, or Firm—Antonelli, Terry, Stout and Kraus, LLP (57) ABSTRACT

An object of the present invention is to obtain an apparatus and a method for the detection of chemical agents which are suitable for detecting sulfur mustard and lewisite 1 and are satisfactory from the viewpoint of the speed of detection of chemical agents, the reduction of the rate of wrong information, the specification of the kinds of the chemical agents, and an unmanned continuous-monitoring apparatus. In the present invention, the detecting apparatus comprises a sample introduction section 1 into which a sample is introduced to be heated, an ionization section 2 in which the sample from the sample introduction section is ionized, a mass spectrometry section 3, and a computer 6 for data analysis. When predetermined signals characteristic of sulfur mustard or lewisite 1 are observed, it becomes possible to specify the sample.

33 Claims, 7 Drawing Sheets

FIG. 1

— FLOW OF THE AIR 81
—— CONTROL SIGNAL, DATA 82

APPARATUS AND METHOD FOR DETECTING CHEMICAL AGENTS

BACKGROUND OF THE INVENTION

The present invention relates to an apparatus and a method for the detection of chemical agents, in particular, an apparatus and a method for the detection of chemical agents which are suitable for detecting 2,2'-dichloroethyl sulphide (hereinafter referred to as sulfur mustard) and 2-chlorovinyl-dichloroarsine (hereinafter referred to as lewisite 1) with a mass spectrometer by employing atmospheric pressure chemical ionization (APCI).

In recent years, there has been a desire for an apparatus for detecting chemical agents, for a countermeasure against chemical terrorism including the sarin case. A chemical agent is generally detected by its analysis, and examination by gas chromatography mass spectrometry (GC/MS) is a leading method for the detection. In general, the chemical agent itself is rarely detected in a sample and its presence is proved by detecting a decomposition product capable of remaining easily.

As a prior art regarding another apparatus for analyzing a chemical agent, liquid chromatography mass spectrometry (LC/MS) for the separation and analysis of a volatile or nonvolatile compound is known.

Figure 14:
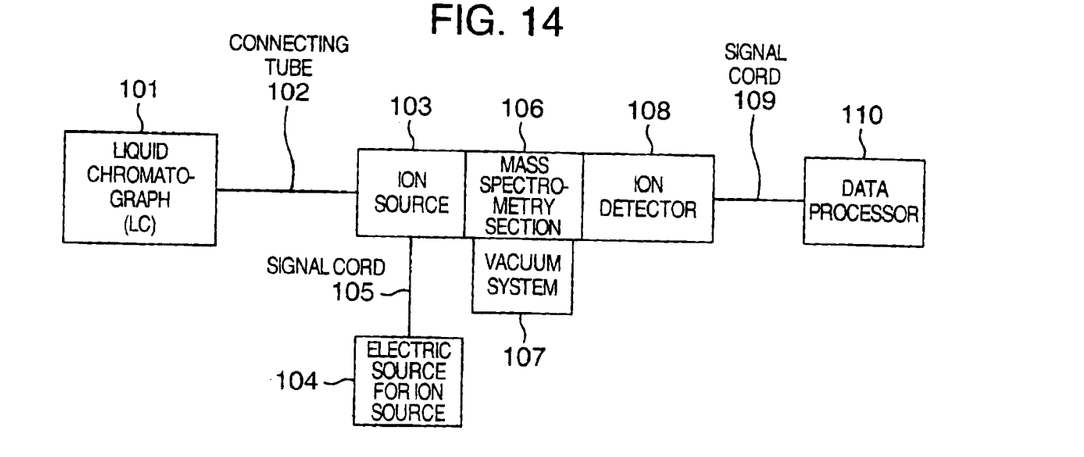
FIG. 14 is a diagram illustrating an outline of the structure of an analyzer according to a prior art in which the liquid chromatography mass spectrometry is employed.

FIG. 14 is a diagram illustrating an outline of the structure of an analyzer according to a prior art, in which the liquid chromatography mass spectrometry is employed. The analyzer according to the prior art is explained below. In FIG. 14, numeral 101 denotes a liquid chromatograph (LC), numeral 102 a connecting tube, numeral 103 an ion source, numeral 104 an electric source for ion source, numerals 105 and 109 signal cords, numeral 106 a mass spectrometry section, numeral 107 a vacuum system, numeral 108 an ion detector, and numeral 110 a data processor.

As shown in FIG. 14, the analyzer according to the prior art, in which the liquid chromatography mass spectrometry is employed, comprises the liquid chromatograph (LC) 101 for separating a sample solution into components, the ion source 103 for producing ions from sample molecules which is controlled by the electric source for ion source 104, the mass spectrometry section 106 for subjecting the produced ions to mass spectrometry which is evacuated by the vacuum system 107, the ion detector 108 for detecting the ions subjected to the mass spectrometry, and the data processor 110 for processing data. The zone comprising the ion source 103, the mass spectrometry section 106 and the ion detector 108 constitutes a mass spectrometry apparatus (MS).

In the above, the sample solution separated into components in the liquid chromatograph (LC) 101 is introduced into the ion source 103 operated at atmospheric pressure, through the connecting tube 102. The ion source 103 is controlled by the electric source for ion source 104 through the signal cord 105 and produces ions from sample molecules in the sample solution. Then, the produced ions are introduced into the mass spectrometry section 106 and subjected to mass spectrometry. The mass spectrometry section 106 has been evacuated by the vacuum system 107. The ions subjected to the mass spectrometry are detected by the ion detector 108. The signals obtained by the detection are sent to the data processor 110 through the signal cord 109 to give analytical data such as a mass spectrum or a chromatogram.

The mass spectrometry apparatus in the analyzer composed as described above requires an interface means between the mass spectrometry apparatus and the liquid chromatograph (LC) 101 because ions have to be treated in a vacuum in the apparatus. That is, LC is an apparatus in which a large volume of water or an organic solvent is treated at atmospheric pressure, while MS is an apparatus in which ions are treated in a high vacuum. Therefore, direct connection of these two apparatus with each other has been considered difficult.

A method called Ion Mobility Spectrometry is mainly a method comprising a combination of the ionization of a sample by means of a radiation source and the measurement of the mobility of ions in an electric field. This method is a leading method for on-the-spot detection, and many products employing this method have been produced in Europe and America. The Ion Mobility Spectrometry method is often adopted for many purposes including military purposes because it permits miniaturization of a detector as compared with GC/MS and LC/MS. However, in Ion Mobility Spectrometry, a sample is not distinguished by mass-to-charge ratio (mass number of ion/valence of ion), so that the display of a detection result is rough. Therefore, it is prescribed that soldiers have to carry a detector in order to wear a protective mask when an alarm is sounded.

As a prior art regarding the Ion Mobility Spectrometry method, there is known, for example, the technique disclosed in U.S. Pat. No. 6,225,623 B1.

The prior arts described above involve the following problems. An electronic ionization (EI) technique tends to decompose a substance to be detected because it applies a high energy to the substance itself. In a detecting apparatus employing GC/MS, ions having a molecular weight higher than that of a substance to be detected are difficult to monitor, so that it is difficult to specify a sample. GC and LC treatments for separating a substance to be detected extend the detection time.

The Ion Mobility Spectrometry method does not makes it possible to specify the kind of a chemical agent and is disadvantageous in that it responds to various compounds, resulting in difficult judgment on a sample to be subjected to detection and a high rate of wrong information. As described above, when the Ion Mobility Spectrometry method is adopted, the sample is difficult to specify and the rate of wrong information is high.

An object of the present invention is to solve such problems in the prior arts and provide an apparatus and a method for the detection of chemical agents which are suitable for detecting sulfur mustard and lewisite 1 and are satisfactory from the viewpoint of the speed of detection of chemical agents, the reduction of the rate of wrong information, the specification of the kinds of the chemical agents, and an unmanned continuous-monitoring apparatus.

SUMMARY OF THE INVENTION

According to the present invention, the above object can be achieved by providing an ion source into which a test sample is introduced and in which a preset temperature at which the test sample is positively or negatively ionized therein by corona discharge is 110° C. to 180° C.; and a mass spectrometry section where the ions produced in said ion source are subjected to mass spectrometry, and by detecting signals due to a chemical agent to be detected.

In addition, the above object can be achieved by providing an ion source into which a test sample is introduced and in which a preset temperature at which the test sample is positively or negatively ionized therein by corona discharge is 110° C. to 180° C.; a mass spectrometry section where the ions produced in said ion source are subjected to mass spectrometry; and a means for monitoring ionic strength due to a chemical agent to be detected.

Further, the above object can be achieved by providing an ion source into which a test sample is introduced and in which a preset temperature at which the test sample is positively or negatively ionized therein by corona discharge is 110° C. to 180° C.; a mass spectrometry section where the ions produced in said ion source are subjected to mass spectrometry; and a means for monitoring the ionic strength of ions having mass-to-charge ratio (mass number of ion/valence of ion) values corresponding to a chemical agent to be detected.

Still further, the above object can be achieved by providing a sample introduction section into which a test sample is introduced and in which a preset temperature at which the test sample is heated therein is 110° C. to 180° C.; an ion source where a preset temperature at which the gas produced by the heating is positively or negatively ionized therein by corona discharge is 110° C. to 180° C.; and a mass spectrometry section where the ions produced in said ion source are subjected to mass spectrometry, and by detecting signals due to a chemical agent to be detected.

Still further, the above object can be achieved by providing a sample introduction section into which a test sample is introduced and in which a preset temperature at which the test sample is heated therein is 110° C. to 180° C.; an ion source where a preset temperature at which the gas produced by the heating is positively or negatively ionized therein by corona discharge is 110° C. to 180° C.; a mass spectrometry section where the ions produced in said ion source are subjected to mass spectrometry; and a means for monitoring ionic strength due to a chemical agent to be detected.

Still further, the above object can be achieved by providing a sample introduction section into which a test sample is introduced and in which a preset temperature at which the test sample is heated therein is 110° C. to 180° C.; an ion source where a preset temperature at which the gas produced by the heating is positively or negatively ionized therein by corona discharge is 110° C. to 180° C.; a mass spectrometry section where the ions produced in said ion source are subjected to mass spectrometry; and a means for monitoring the ionic strength of ions having mass-to-charge ratio (mass number of ion/valence of ion) values corresponding to a chemical agent to be detected.

In the above, the aforesaid ion source is constructed so as to employ backflow type atmospheric pressure chemical ionization (APCI) in which the test sample from the aforesaid sample introduction section is introduced into a place between a corona discharge occurrence portion and the mass spectrometry section and flows toward the corona discharge occurrence portion opposite to the mass spectrometry section.

The present invention using the above-mentioned means makes it possible to specify chemical agents and reduce the rate of wrong information and is suitable for detecting, in particular, sulfur mustard and lewisite 1. The detection of chemical agents employing the backflow type atmospheric pressure chemical ionization (APCI), in which the test sample from the sample introduction section is introduced into a place between the corona discharge occurrence portion and the mass spectrometry section and flows toward the corona discharge occurrence portion opposite to the mass spectrometry section, is characteristic of the present invention.

Other objects, features and advantages of the invention will become apparent from the following description of the embodiments of the invention taken in conjunction with the accompanying drawings.

DETAILED DESCRIPTION OF THE INVENTION

Embodiments of the apparatus and method for detecting chemical agents of the present invention are explained below in detail with reference to the drawings.

Figure 1:
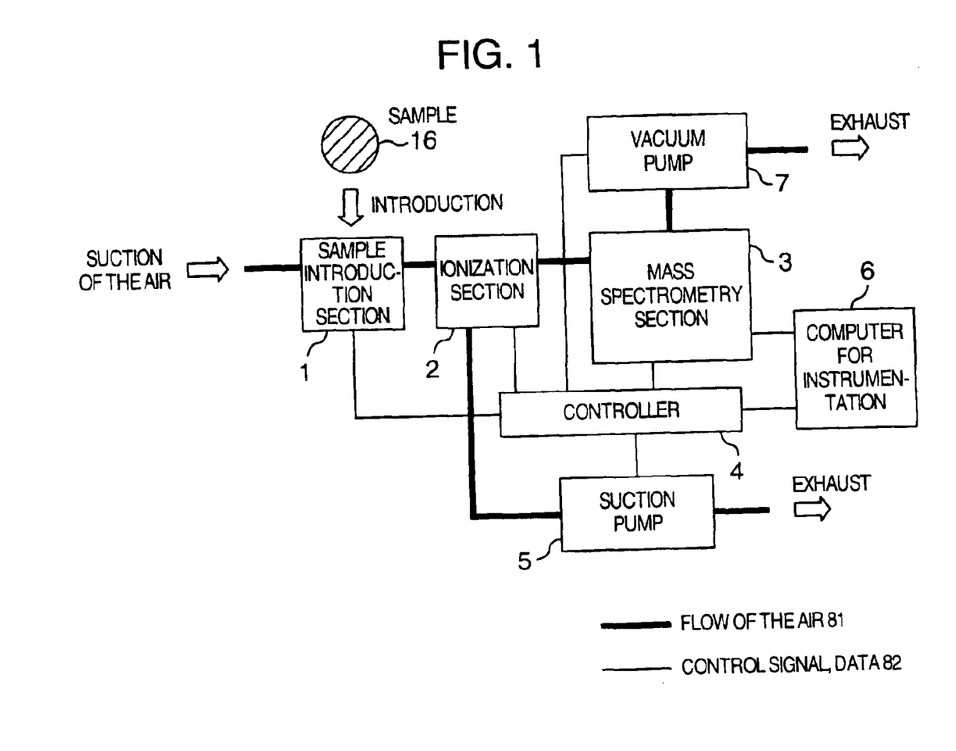
FIG. 1 is a block diagram showing an outline of the structure of an apparatus for detecting chemical agents according to one embodiment of the present invention.

FIG. 1 is a block diagram showing an outline of the structure of an apparatus for detecting chemical agents according to one embodiment of the present invention. In FIG. 1, numeral 1 denotes a sample introduction section, numeral 2 an ionization section, numeral 3 a mass spectrometry section, numeral 4 a controller, numeral 5 a suction pump, numeral 6 a computer for instrumentation, numeral 7 a vacuum pump, and numeral 16 a sample.

As shown in FIG. 1, the apparatus for detecting chemical agents according to the embodiment of the present invention comprises the sample introduction section 1, the ionization section 2 as ion source, the mass spectrometry section 3, the controller 4, the suction pump 5, the computer for instrumentation 6 and the vacuum pump 7. In the thus constructed apparatus for detecting chemical agents, the sample 16 having fine particles of a hazardous material adhering thereto which has been introduced into the sample introduction section 1 is gasified by heating by a heating mechanism (not shown) provided in the sample introduction section 1. The gasified sample is introduced into the ionization section 2 by a flow of the air 81 (shown by the thick line in FIG. 1) sucked by the suction pump 5. The suction pump 5 has a function of discharging the air sucked and a function of making the volume of the air sucked variable in the range of 0 to 2 liters/min by means of a mass flow controller.

The test sample introduced into the ionization section 2 as ion source is sent to a corona discharge region at the pointed end of the cat whisker for corona discharge described hereinafter, and is positively ionized depending on the kinds of one or more components to be detected, by a high positive voltage (approximately 2 kV to 5 kV) applied to the cat whisker. Only the positively ionized component(s) are introduced into the mass spectrometry section 3 through a first small hole provided in the ionization section 2, by an electric field applied to the region extending from the ionization section 2 to the mass spectrometry section 3. In this case, surplus substances other than ions and molecules which pass through the first small hole in the ionization section 2 are discharged from the ionization section 2 by the suction pump 5 and then discharged from the apparatus. The adsorption of the sample on the inner wall of a path for sample introduction between the sample introduction section 1 and the ionization section 2 and on the inside of the ionization section 2 can be prevented by maintaining the path for sample introduction and the ionization section 2 at a high temperature.

The ions introduced into the mass spectrometry section 3 pass through a differential exhaust portion in the mass spectrometry section 3 evacuated by the vacuum pump 7, and they are converged by an electrostatic lens system and then subjected to mass spectrometry with a mass spectrometer. The vacuum pump 7 also has a function of keeping the inside of a chamber accommodating the mass spectrometer, at a high vacuum. The ions picked out by the mass spectrometer are converted to electrons by a secondary-electron multiplier in the mass spectrometry section 3, and the current signals thus obtained are amplified by an amplifier and then sent to the computer for instrumentation 6.

The computer for instrumentation 6 conditions the signals input from the mass spectrometry section 3 and displays, for example, the relationship between mass number/electric charge (mass-to-charge ratio) and ionic strength (mass spectrum), or the change with time of ionic strength at a certain mass-to-charge ratio (mass chromatogram). The final display may be not the above-mentioned mass spectrum or mass chromatogram, but a further simplified display. That is, when the apparatus for detecting chemical agents according to the embodiment of the present invention is used as an apparatus for detecting hazardous materials, it is sufficient that only whether an undesirable chemical agent has been detected or not is displayed.

The controller 4 performs on/off control of the functional sections constituting the detecting apparatus, setting of temperature/voltage/vacuum pressure, status monitoring, and the like. Such connections are indicated by the control signal, data 82 shown by the thin lines in FIG. 1.

As described above, according to the embodiment of the present invention, it becomes possible to analyze fine particles of a hazardous material adhering to the sample 16 introduced into the sample introduction section 1, in the mass spectrometry section 3.

Figure 2:
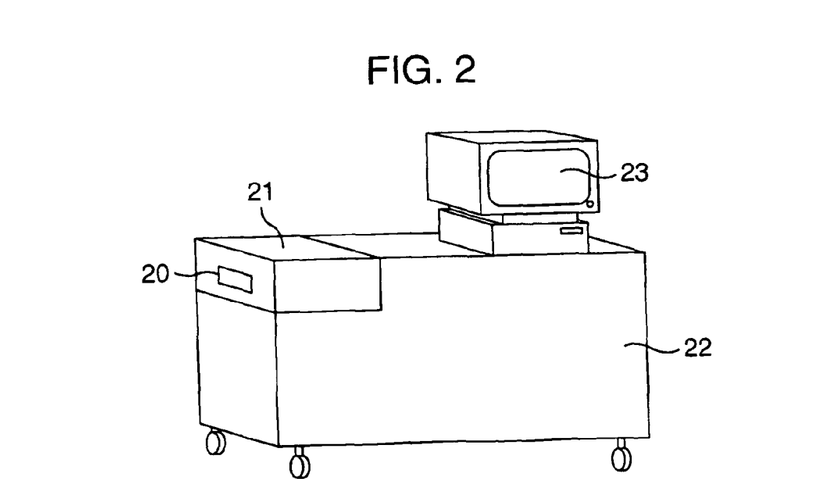
FIG. 2 is a perspective view showing the appearance of the detecting apparatus according to the embodiment of the present invention.

FIG. 2 is a perspective view showing the appearance of the detecting apparatus according to the embodiment of the present invention. As shown in FIG. 2, the detecting apparatus is composed of a filter paper heating section 21 having a filter paper inlet 20, an analysis section 22 and a display section 23, and can be moved owing to wheels located in the lowermost part of the apparatus.

During the production or transportation of a chemical agent, a very slight amount of the chemical agent usually adheres to the hands, skin, clothes and the like of a person who is handling the chemical agent. When this person handles his or her personal effects such as a bag, the chemical agent adheres also to the personal effects.

Therefore, in the embodiment of the present invention, the surface of, for example, a bag as an object of examination (a substance subjected to detection) is wiped with a clean and soft material (e.g. cloth or filter paper) (which is hereinafter referred to as test paper but needs not always be paper), and a chemical agent adhering to the test paper is analyzed. That is, the test paper having the chemical agent adhering thereto is inserted into the filter paper heating section 21 through the filter paper inlet 20. Since the test paper is heated in the filter paper heating section 21, the chemical agent adhering to the test paper is vaporized, and then analyzed by the analysis section 22. The analysis section is accommodating the detecting apparatus having the structure explained with reference to FIG. 1 and is equipped with a database in which information concerning signals due to the chemical agent has been registered. When the detection of predetermined signals characteristic of the chemical agent is confirmed by the analysis result and the information registered in the database, the computer for instrumentation 6 displays a warning in the display section 23.

Figure 3:
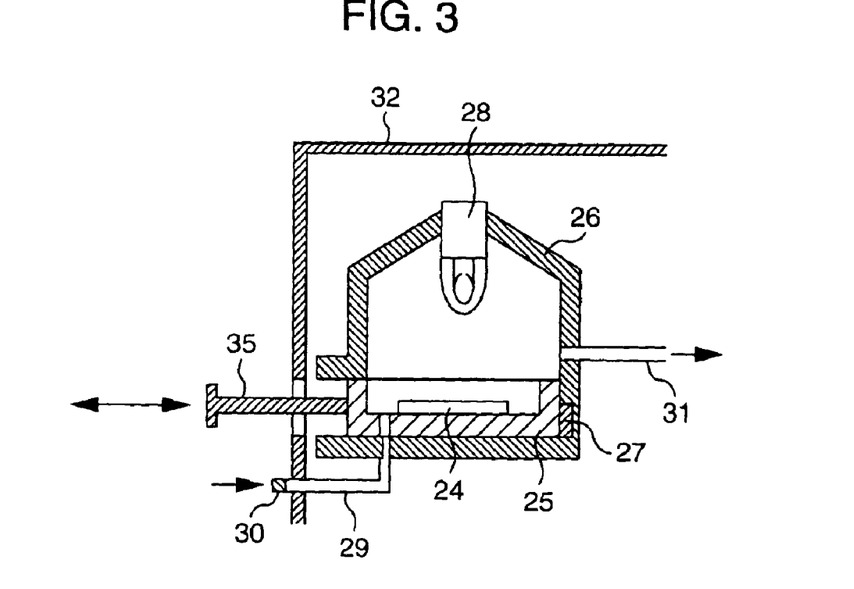
FIG. 3 is a cross-sectional view showing an example of the structure of the filter paper heating section (an oven) shown in FIG. 2.

FIG. 3 is a cross-sectional view showing an example of the structure of the filter paper heating section (an oven) shown in FIG. 2. In FIG. 3, numeral 24 denotes a filter paper, numeral 25 a tray, numeral 25' a grip, numeral 26 a tray holder, numeral 27 a sensor, numeral 28 a halogen lamp, numeral 29 an air inlet tube, numeral 30 a filter, numeral 31 a sample inlet tube, and numeral 32 a cover.

The filter paper heating section (the oven) 21 is composed of the tray holder 26, the halogen lamp 28 provided as a heat source in the tray holder 26, and the tray 25 on which the filter paper 24 is set. In the filter paper heating section 21 thus composed, the filter paper 24, a test paper with which an object of examination has been wiped is set on the tray 25 of slide type at first. The tray 25 having the filter paper 24 set thereon is inserted into the tray holder 26. When the sensor 27 senses that the tray 25 has been inserted to be set in a predetermined position, the halogen lamp provided in the upper part of the tray holder 26 is lighted. The filter paper 24 is heated by heat rays from the halogen lamp 28, and materials adhering to the filter paper 24 are vaporized. The heating temperature is preferably 100° C. or higher. The sample thus produced from the filter paper 24 is sent to the analysis section 22 through the sample inlet tube 31 together with air introduced into the tray holder 26 through the air inlet tube 29.

The air inlet tube 29 is preferably equipped with the filter 30 for removing dust and the like. For safety, the filter paper heating section 21 is preferably equipped with the cover 32 and the grip 25' which have thermal insulating properties, because its temperature becomes high. The sample introduction section 1 may be such that a test sample (a substance to be subjected to detection) sucked from the outside is directly introduced into the ionization section 2.

Figure 4:
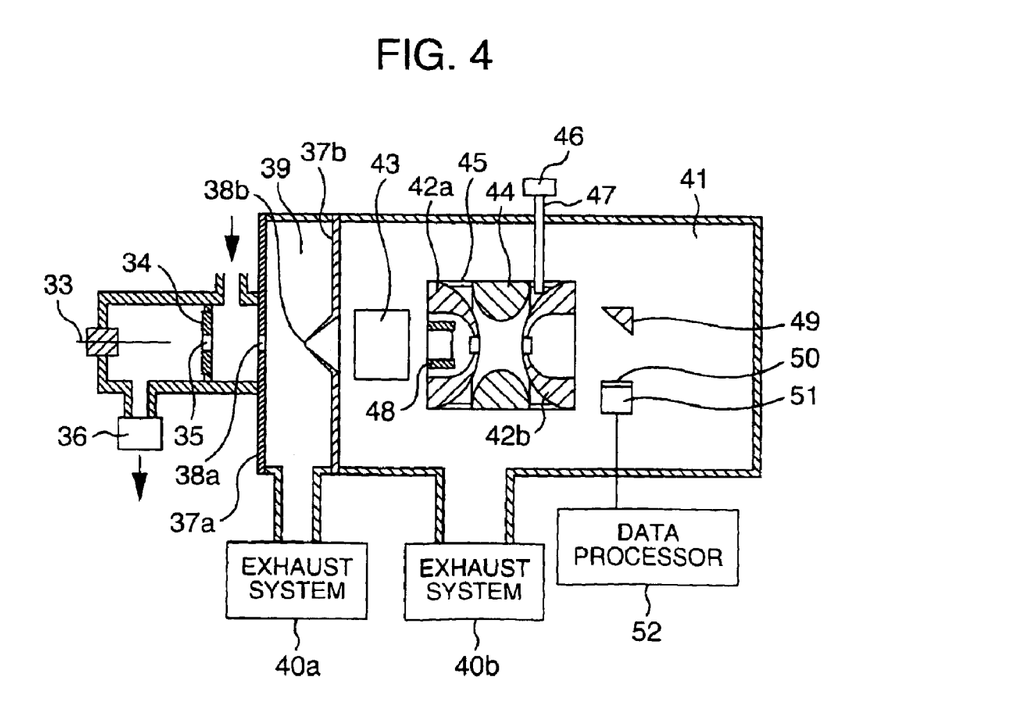
FIG. 4 is a block diagram showing examples of the structures of the ionization section and mass spectrometry section of the detecting apparatus according to the embodiment of the present invention.

FIG. 4 is a block diagram showing examples of the structures of the ionization section and mass spectrometry section of the detecting apparatus according to the embodiment of the present invention. In FIG. 4, numeral 33 denotes a cat whisker, numeral 34 a counter electrode, numeral 35 an opening, numeral 36 a suction pump, numerals 37a and 37b small-hole-provided electrodes, numeral 38a a first small hole for ion introduction, numeral 38b a second small hole for ion introduction, numeral 39 a differential exhaust portion, numerals 40a and 40b exhaust systems, numeral 41 a vacuum portion, numerals 42a and 42b end cap electrodes, numeral 43 an ion-converging lens, numeral 44 a ring electrode, numeral 45 a quartz ring, numeral 46 a gas feeder, numeral 47 a gas inlet tube, numeral 48 a gate electrode, numeral 49 a conversion electrode, numeral 50 a scintillator, numeral 51 a photomultiplier, and numeral 52 a data processor.

In FIG. 4, the cat whisker 33 is located in the ionization section 2, and a high voltage is applied between the cat whisker 33 and the counter electrode 34. By this application, corona discharge is caused near the pointed end of the cat whisker 33, so that nitrogen, oxygen, water vapor and the like are ionized at first. The ions thus formed are called primary ions. The primary ions move toward the counter electrode 34 owing to an electric field. The test sample supplied from the sample introduction section to the region between the counter electrode 34 and the small-hole-provided electrode 37a through the sample inlet tube 31 flows toward the cat whisker 33 through the opening 35 provided in the counter electrode 34 in the ionization section 2, owing to the suction pump 36, and is ionized by reaction with the primary ions.

There is an electric potential difference of about 1 kV between the counter electrode 34 and the small-hole-provided electrode 37a. Therefore, the ions formed by the reaction move toward the small-hole-provided electrode 37a and are introduced into the differential exhaust portion 39 through the small hole 38a. Adiabatic expansion takes place in the differential exhaust portion 39, resulting in so-called clustering, i.e., the adhesion of solvent molecules and the like to the ions. For reducing the clustering, the small-hole-provided electrodes 37a and 37b are preferably heated with a heater or the like.

When the ionization section 2 having the structure shown in FIG. 4 is used, the primary ions formed by the corona discharge move toward the counter electrode 34 owing to the electric potential difference between the cat whisker 33 and the counter electrode 34 and then move toward the small-hole-provided electrode 37a through the opening 35. Since the test sample from the sample introduction section is supplied to the region between the counter electrode 34 and the small-hole-provided electrode 37a, the reaction of the primary ions with the test sample takes place. Neutral molecules and the like produced by the corona discharge flow toward the cat whisker 33 from the counter electrode 34 owing to the suction pump 36 and hence are removed from the corona discharge portion. In addition, the neutral molecules and the like hardly flow into the region where the ionization reaction between the primary ions and the sample takes place. By thus separating the region for the formation of the primary ions by the corona discharge and the region for the ionization reaction between the primary ions and the sample to prevent the radical neutral molecules produced by the corona discharge from flowing into the ionization region, the decomposition of the sample in the ionization region can be reduced.

As described above, in the embodiment of the present invention, the primary ions are formed by utilizing the corona discharge in the air and the test sample is ionized by utilizing the chemical reaction of the primary ions with the test sample. This method is called an atmospheric pressure chemical ionization method. In the case of sulfur mustard, there is employed a positive ionization mode in which positive ions are formed by applying a high positive voltage to the cat whisker 33. In this case, the primary ions are often ions of water molecules $[(H_2O)^+]$. A typical positive ionization reaction can be represented by the following formulas:

$$M+(H_2O)^+ \rightarrow M^+ +(H_2O), \quad M^+ +H \rightarrow (M+H)^+$$

wherein M is a molecule of a substance to be detected and H is a hydrogen atom.

In the case of lewisite 1, there is employed a negative ionization mode in which negative ions are formed by applying a high negative voltage to the cat whisker 33. In this case, the primary ions are often ions of oxygen molecules $[(O_2)^-]$. A typical negative ionization reaction is shown below:

$$M+(O_2)^- \rightarrow (M)^- + O_2$$

wherein M is a molecule in a gas.

The ions formed as described above are introduced into the vacuum portion 41 evacuated by the exhaust system 40b, through the first small hole for ion introduction 38a of the small-hole-provided electrode 37a, the differential exhaust portion 39 evacuated by the exhaust system 40a, and the second small hole for ion introduction 38b of the small-hole-provided electrode 37b. A voltage called a drift voltage is applied between the small-hole-provided electrodes 37a and 37b. This drift voltage is effective in improving the ion permeability of the second small hole for ion introduction 38b by drifting the ions introduced into the differential exhaust portion 39, toward the small hole for ion introduction 38b, and is effective also in releasing solvent (e.g. water) molecules adhering to the ions, by collision between the ions and gas molecules remaining in the differential exhaust portion 39. A voltage is further applied to the small-hole-provided electrode 37b. This voltage affects energy at the time of passage of the ions through the opening provided in the end cap electrode 42a (incident energy).

Since the efficiency of ion trapping of an ion trap mass spectrometer used in the embodiment of the present invention is dependent on the incident energy of the ions, the above-mentioned voltage is set so as to improve the efficiency of trapping. The ions introduced into the vacuum portion 41 are converged by the ion-converging lens 43 and then introduced into the ion trap mass spectrometer composed of the end cap electrodes 42a and 42b and the ring electrode 44. The end cap electrodes 42a and 42b and the ring electrode 44 are held by the quartz ring 45.

A gas for collision such as helium is introduced into the mass spectrometer from the gas feeder 46 through the gas inlet tube 47. The gate electrode 48 is provided in order to control the timing of introduction of the ions into the ion trap mass spectrometer. The ions discharged from the mass spectrometer after mass spectrometry are detected by a detector composed of the conversion electrode 49, the scintillator 50 and the photomultiplier 51. The ions collide with the conversion electrode 49 to which a voltage for accelerating the ions is being applied. Charged particles are liberated from the surface of the conversion electrode 49 by the collision of the ions with the conversion electrode 49. The charged particles are detected by the scintillator 50 and the resulting signals are amplified by the photomultiplier 51. The signals detected are sent to the data processor 52. Although an explanation is given above by taking the case where the ion trap mass spectrometer is used, a quadrupole mass spectrometer may be used.

The data processor 52 identifies ions having mass-to-charge ratio values corresponding to a chemical agent to be detected (for example, positive ions having mass-to-charge ratio values corresponding to sulfur mustard, or negative ions having mass-to-charge ratio values corresponding to lewisite 1), and determines the signal strength due to the ions to judge whether the chemical agent to be detected, i.e., sulfur mustard or lewisite 1 has been detected or not. When sulfur mustard or lewisite 1 has been detected, the data processor 52 displays both a warning and the kind of the detected chemical agent in the display section 23. The warning may be given also by giving a loud sound or switching on and off a red warning lamp, in order to attract attention.

Figure 5:
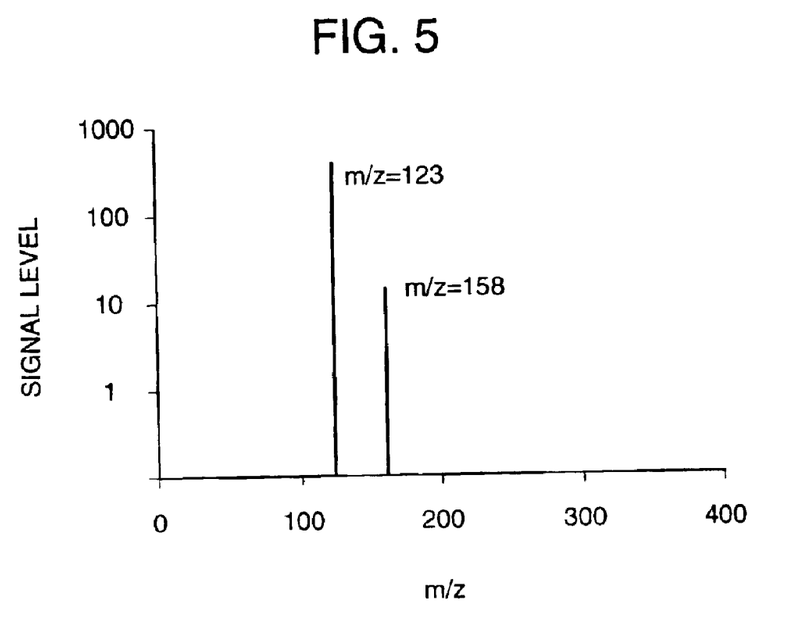
FIG. 5 is a graph illustrating a mass spectrum of sulfur mustard obtained according to the embodiment of the present invention.

FIG. 5 is a graph illustrating a mass spectrum of sulfur mustard obtained according to the embodiment of the present invention. The graph is obtained when sulfur mustard vapor is directly introduced into the sample introduction section and the following conditions are employed: the detection of positive ions, a drift voltage of 50 V, a temperature of the ionization section of 150° C., and a temperature of the sample introduction section of 180° C.

In this case, as shown in FIG. 5, signals at mass-to-charge ratio values of 123 and 158, respectively, were detected. Since sulfur mustard has a molecular weight $M_{HD}$ of 158 or 160, the signal at a mass-to-charge ratio value of 123 is due to $(M_{HD}-Cl)^+$ and the signal at a mass-to-charge ratio value of 158 is due to $(M_{HD})^+$. That is, when both of the signals at mass-to-charge ratio values of 123 and 158 are detected, it is judged that sulfur mustard has been detected. The above detection method can reduce the rate of wrong information. When only the signal at a mass-to-charge ratio value of 123 (or 158) is detected in the case where another component gives the signal at a mass-to-charge ratio value of 123 (or 158) by accident, judgment that sulfur mustard has been detected gives wrong information in some cases.

Figure 6:
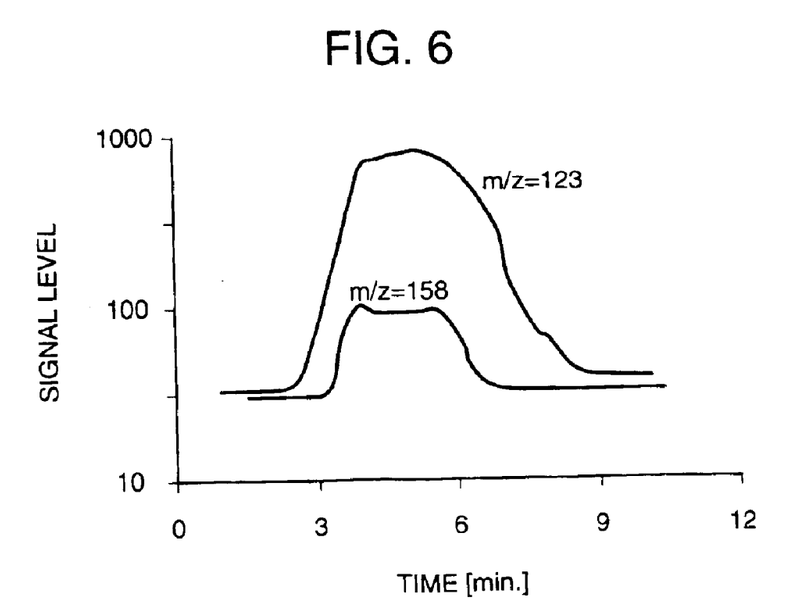
FIG. 6 is a graph illustrating characteristics at a sample introduction section temperature of 110° C. and an ion source temperature of 110° C. of signals at mass-to-charge ratio values of 123 and 158, respectively, detected by the introduction of sulfur mustard as a sample.
Figure 7:
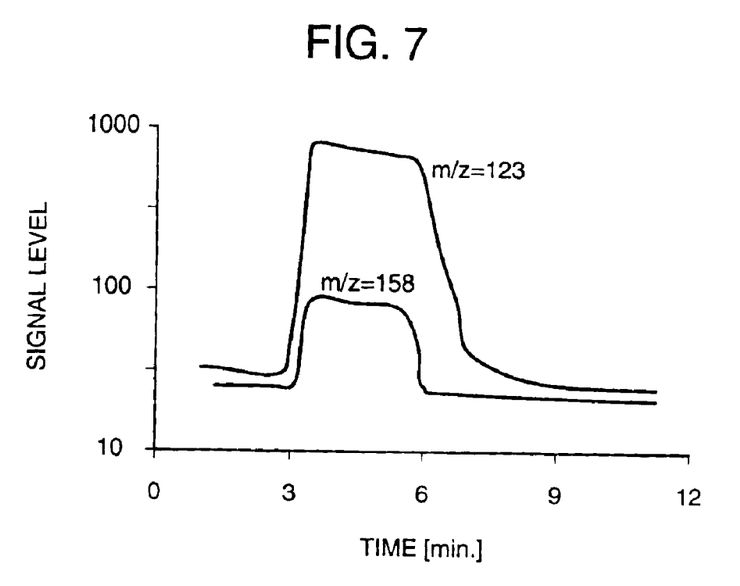
FIG. 7 is a graph illustrating characteristics at a sample introduction section temperature of 180° C. and an ion source temperature of 150° C. of signals at mass-to-charge ratio values of 123 and 158, respectively, detected by the introduction of sulfur mustard as a sample.

FIGS. 6 and 7 are graphs illustrating the temperature dependence of signals at mass-to-charge ratio values of 123 and 158, respectively, detected by the introduction of sulfur mustard as a sample. The case shown in FIG. 6 is the changes with time of ionic strength signal level at a sample introduction section temperature of 110° C. and an ion source temperature of 110° C. observed when sulfur mustard gas is sucked for a definite time and then the sucking is stopped. The sample introduction section was composed of a SUS piping having a temperature-controlling ability. The case shown in FIG. 7 is the changes with time of ionic strength signal level at a sample introduction section temperature of 180° C. and an ion source temperature of 150° C. observed when sulfur mustard gas is sucked for a definite time and then the sucking is stopped. The sample introduction section was composed of a SUS piping having a temperature-controlling ability.

When the sample introduction section and the ion source are set at high temperatures, respectively, there is a possibility that the adsorption of the sample might be reduced, resulting in faster arrival of sulfur mustard gas at the ion source. The setting at high temperatures is effective in reducing the signal level rising time extending from the gas suction to the signal detection, and in reducing the signal level dropping time extending from the stopping of the gas suction to the return of the signal level to the background level.

Figure 8:
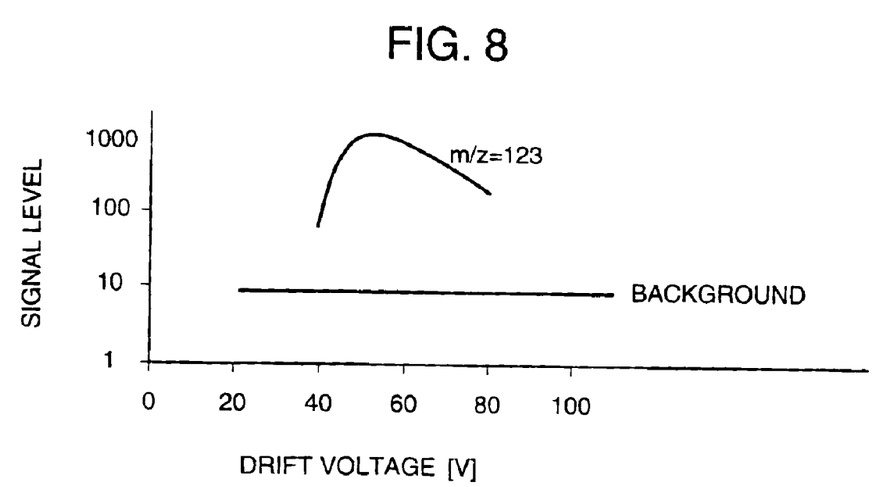
FIG. 8 is a graph illustrating the drift voltage dependence of a signal at a mass-to-charge ratio value of 123 detected by the introduction of sulfur mustard as a sample.

FIG. 8 is a graph illustrating the drift voltage dependence of a signal at a mass-to-charge ratio value of 123 detected by the introduction of sulfur mustard as a sample. As can be seen from FIG. 8, a signal level higher than the background level can be attained at a drift voltage of not more than 80 V and more than 40 V. The term "background level" means the level of a signal at a mass-to-charge ratio value of 123 attained when no sulfur mustard is introduced as a sample. Whether sulfur mustard has been detected or not is judged by monitoring signals on a level higher than the background level. Accordingly, a higher signal level can be attained by setting the drift voltage at 50 V to 80 V.

Figure 9:
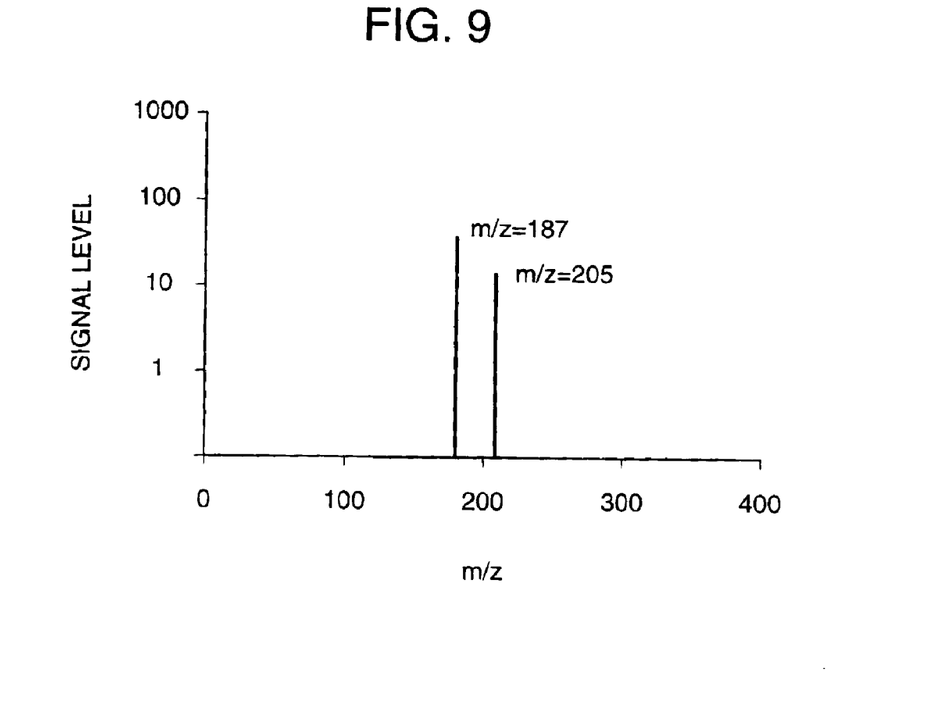
FIG. 9 is a graph illustrating a mass spectrum of lewisite 1 obtained according to the embodiment of the present invention.

FIG. 9 is a graph illustrating a mass spectrum of lewisite 1 obtained according to the embodiment of the present invention. The graph is obtained when lewisite 1 vapor is directly introduced into the sample introduction section and the following conditions are employed: the detection of negative ions, a drift voltage of −40 V, a temperature of the ionization section of 180° C., and a temperature of the sample introduction section of 180° C.

In this case, as shown in FIG. 9, signals at mass-to-charge ratio values of 187 and 205, respectively, were detected. Since lewisite 1 has a molecular weight $M_L$ of 206 or 208, the signal at a mass-to-charge ratio value of 205 is due to $(M_L-H)^+$ and the signal at a mass-to-charge ratio value of 187 is due to a decomposition product of lewisite 1. That is, when both of the signals at mass-to-charge ratio values of 187 and 205 are detected, it is judged that lewisite 1 has been detected. The above detection method can reduce the rate of wrong information. When only the signal at a mass-to-charge ratio value of 187 (or 205) is detected in the case where another component gives the signal at a mass-to-charge ratio value of 187 (or 205) by accident, judgment that lewisite 1 has been detected gives wrong information in some cases.

Figure 10:
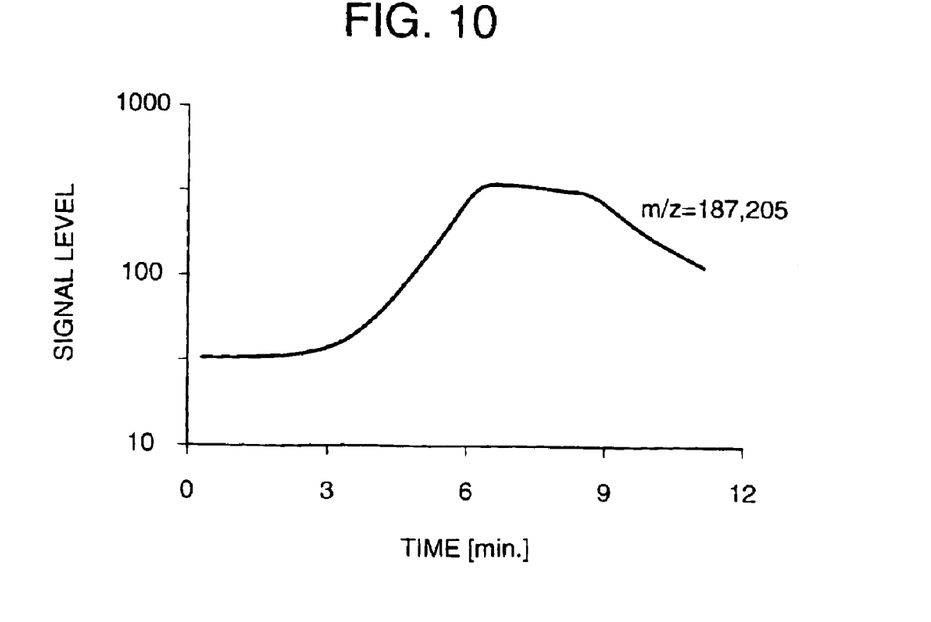
FIG. 10 is a graph illustrating characteristics at a sample introduction section temperature of 30° C. and an ion source temperature of 110° C. of signals at mass-to-charge ratio values of 187 and 205, respectively, detected by the introduction of lewisite 1 as a sample.
Figure 11:
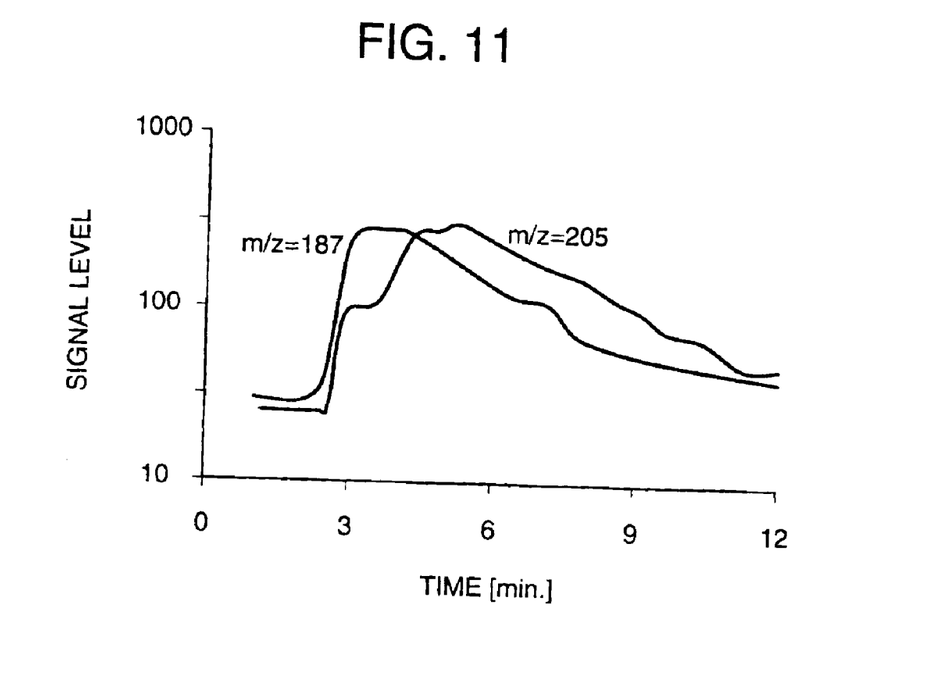
FIG. 11 is a graph illustrating characteristics at a sample introduction section temperature of 110° C. and an ion source temperature of 110° C. of signals at mass-to-charge ratio values of 187 and 205, respectively, detected by the introduction of lewisite 1 as a sample.
Figure 12:
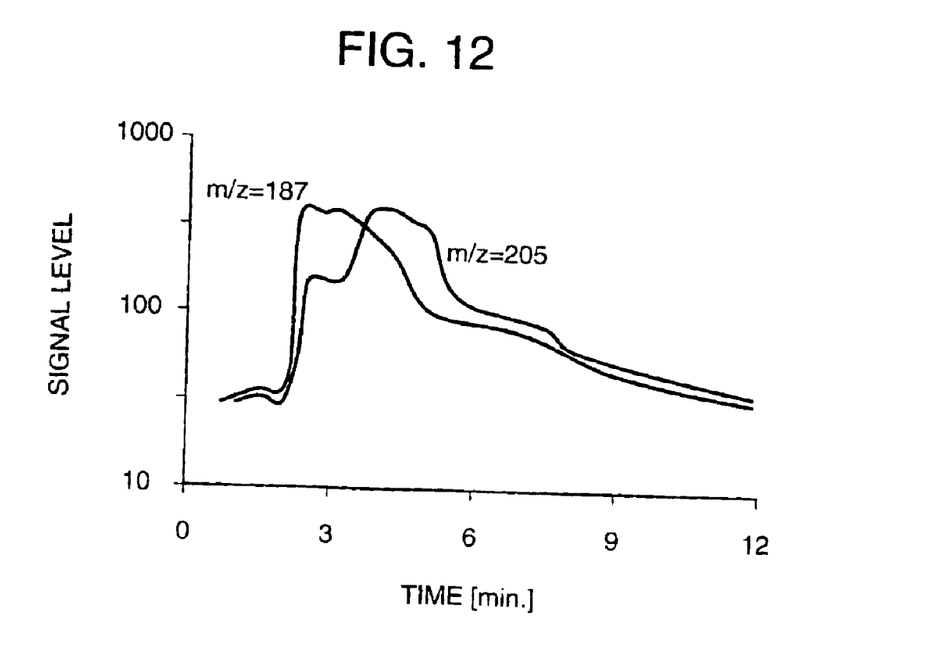
FIG. 12 is a graph illustrating characteristics at a sample introduction section temperature of 180° C. and an ion source temperature of 150° C. of signals at mass-to-charge ratio values of 187 and 205, respectively, detected by the introduction of lewisite 1 as a sample.

FIGS. 10 to 12 are graphs illustrating the temperature dependence of signals at mass-to-charge ratio values of 187 and 205, respectively, detected by the introduction of lewisite 1 as a sample. The case shown in FIG. 10 is the change with time of ionic strength signal level at a sample introduction section temperature of 30° C. and an ion source temperature of 110° C. observed when lewisite 1 gas is sucked for a definite time and then the sucking is stopped. The sample introduction section was composed of a Teflon (a registered trade name) piping. The case shown in FIG. 11 is the changes with time of ionic strength signal level at a sample introduction section temperature of 110° C. and an ion source temperature of 110° C. observed when lewisite 1 gas is sucked for a definite time and then the sucking is stopped. The sample introduction section was composed of a SUS piping having a temperature-controlling ability. The case shown in FIG. 12 is the changes with time of ionic strength signal level at a sample introduction section temperature of 180° C. and an ion source temperature of 150° C. observed when lewisite 1 gas is sucked for a definite time and then the sucking is stopped. The sample introduction section was composed of a SUS piping having a temperature-controlling ability.

When the sample introduction section and the ion source are set at high temperatures, respectively, there is a possibility that the adsorption of the sample might be reduced, resulting in faster arrival of lewisite 1 gas at the ion source. The setting at high temperatures is effective in reducing the signal level rising time extending from the gas suction to the signal detection, and in reducing the signal level dropping time extending from the stopping of the gas suction to the return of the signal level to the background level.

Figure 13:
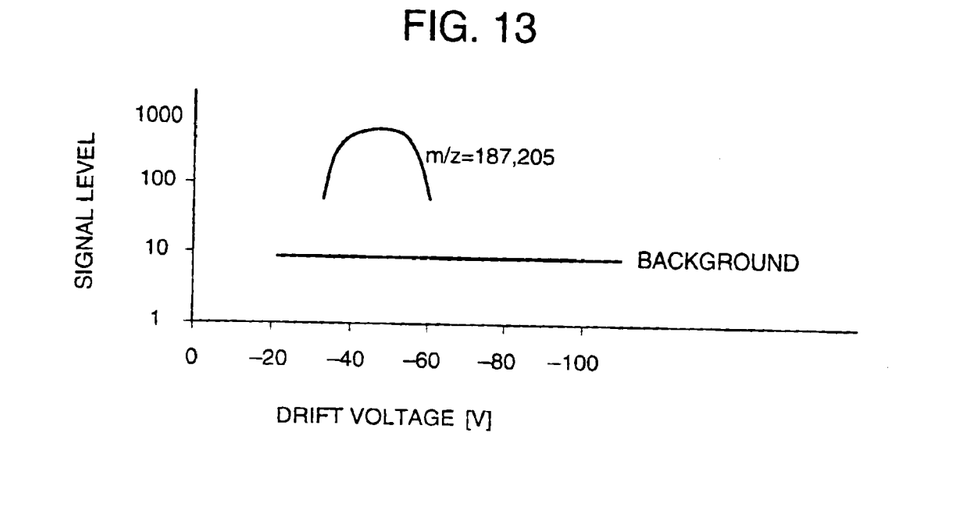
FIG. 13 is a graph illustrating the drift voltage dependence of signals at mass-to-charge ratio values of 187 and 205, respectively, detected by the introduction of lewisite 1 as a sample.

FIG. 13 is a graph illustrating the drift voltage dependence of signals at mass-to-charge ratio values of 187 and 205, respectively, detected by the introduction of lewisite 1 as a sample. As can be seen from FIG. 13, a signal level higher than the background level can be attained at a drift voltage in the range of −30 V to −60 V. The term "background level" means the level of signals at mass-to-charge ratio values of 187 and 205 attained in the case where no lewisite 1 is introduced as a sample. Whether lewisite 1 has been detected or not is judged by monitoring signals on a level higher than the background level. Accordingly, a higher signal level can be attained by setting the drift voltage at −30 V to −60 V.

As explained above, according to the present invention, the presence of sulfur mustard or lewisite 1 can easily be judged by sucking a test sample and confirming mass-to-charge ratio in the analysis section of the detecting apparatus [atmospheric pressure chemical ionization (APCI)-mass spectrometer (MS)].

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. An apparatus for detecting chemical agents comprising an ion source into which a test sample is introduced and in which a preset temperature at which the test sample is positively ionized therein by corona discharge is 110° C. to 180° C.; and a mass spectrometry section where the ions produced in said ion source are subjected to mass spectrometry, wherein signals due to a chemical agent to be detected are detected.

2. An apparatus for detecting chemical agents comprising an ion source into which a test sample is introduced and in which a preset temperature at which the test sample is positively ionized therein by corona discharge is 110° C. to 180° C.; a mass spectrometry section where the ions produced in said ion source are subjected to mass spectrometry; and a means for monitoring ionic strength due to a chemical agent to be detected.

3. An apparatus for detecting chemical agents comprising an ion source into which a test sample is introduced and in which a preset temperature at which the test sample is positively ionized therein by corona discharge is 110° C. to 180° C.; a mass spectrometry section where the ions produced in said ion source are subjected to mass spectrometry; and a means for monitoring the ionic strength of ions having mass-to-charge ratio (mass number of ion/valence of ion) values corresponding to a chemical agent to be detected.

4. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is positively ionized therein by corona discharge is 110° C. to 180° C.; and a mass spectrometry section where the ions produced in said ion source are subjected to mass spectrometry, wherein signals due to a chemical agent to be detected are detected.

5. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is positively ionized therein by corona discharge is 110° C. to 180° C.; a mass spectrometry section where the ions produced in said ion source are subjected to mass spectrometry; and a means for monitoring ionic strength due to a chemical agent to be detected.

6. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is positively ionized therein by corona discharge is 110° C. to 180° C.; a mass spectrometry section where the ions produced in said ion source are subjected to mass spectrometry; and a means for monitoring the ionic strength of ions having mass-to-charge ratio (mass number of ion/valence of ion) values corresponding to a chemical agent to be detected.

7. An apparatus for detecting chemical agents according to any one of claims 1 to 6, wherein the aforesaid ion source is constructed so as to employ backflow type atmospheric pressure chemical ionization (APCI) in which the sample from the aforesaid sample introduction section flows toward a cat whisker capable of causing corona discharge.

8. An apparatus for detecting chemical agents according to any one of claims 1 to 6, wherein a drift voltage applied between small-hole-provided electrodes provided on both sides of the differential exhaust portion of the aforesaid mass spectrometry section is set at 50 V to 80 V.

9. An apparatus for detecting chemical agents according to any one of claims 1 to 6, wherein the aforesaid chemical agent to be detected is 2,2'-dichloroethyl sulphide.

10. An apparatus for detecting chemical agents according to claim 3 or 6, wherein the aforesaid monitoring means monitors the ionic strength of ions having mass-to-charge ratio (mass number of ion/valence of ion) values of 123 and 158, to detect 2,2'-dichloroethyl sulphide.

11. A method for detecting chemical agents which comprises introducing a test sample, heating the test sample at 110° C. to 180° C., positively ionizing the resulting gas by corona discharge, subjecting the resulting ions to mass spectrometry, and detecting signals due to a chemical agent to be detected.

12. An apparatus for detecting chemical agents comprising an ion source into which a test sample is introduced and in which a preset temperature at which the test sample is negatively ionized therein by corona discharge is 110° C. to 180° C.; and a mass spectrometry section where the ions produced in said ion source are subjected to mass spectrometry, wherein signals due to a chemical agent to be detected are detected.

13. An apparatus for detecting chemical agents comprising an ion source into which a test sample is introduced and in which a preset temperature at which the test sample is negatively ionized therein by corona discharge is 110° C. to 180° C.; a mass spectrometry section where the ions produced in said ion source are subjected to mass spectrometry; and a means for monitoring ionic strength due to a chemical agent to be detected.

14. An apparatus for detecting chemical agents comprising an ion source into which a test sample is introduced and in which a preset temperature at which the test sample is negatively ionized therein by corona discharge is 110° C. to 180° C.; a mass spectrometry section where the ions produced in said ion source are subjected to mass spectrometry; and a means for monitoring the ionic strength of ions haying mass-to-charge ratio (mass number of ion/valence of ion) values corresponding to a chemical agent to be detected.

15. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is negatively ionized therein by corona discharge is 110° C. to 180° C.; and a mass spectrometry section where the ions produced in said ion source are subjected to mass spectrometry, wherein signals due to a chemical agent to be detected are detected.

16. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is negatively ionized therein by corona discharge is 110° C. to 180° C.; a mass spectrometry section where the ions produced in said ion source are subjected to mass spectrometry; and a means for monitoring ionic strength due to a chemical agent to be detected.

17. An apparatus for detecting chemical agents comprising a sample introduction section into which a test sample is introduced and in which a preset temperature at which the test sample is heated therein is 110° C. to 180° C.; an ion source where a preset temperature at which the gas produced by the heating is negatively ionized therein by corona discharge is 110° C. to 180° C.; a mass spectrometry section where the ions produced in said ion source are subjected to mass spectrometry; and a means for monitoring the ionic strength of ions having mass-to-charge ratio (mass number of ion/valence of ion) values corresponding to a chemical agent to be detected.

18. An apparatus for detecting chemical agents according to any one of claims 12 to 17, wherein the aforesaid ion source is constructed so as to employ backflow type atmospheric pressure chemical ionization (APCI) in which the sample from the aforesaid sample introduction section flows toward a cat whisker capable of causing corona discharge.

19. An apparatus for detecting chemical agents according to any one of claims 12 to 17, wherein a drift voltage applied between small-hole-provided electrodes provided on both sides of the differential exhaust portion of the aforesaid mass spectrometry section is set at −30 V to −60 V.

20. An apparatus for detecting chemical agents according to any one of claims 12 to 17, wherein the aforesaid chemical agent to be detected is 2-chlorovinyldichloroarsine.

21. An apparatus for detecting chemical agents according to claim 14 or 17, wherein the aforesaid monitoring means monitors the ionic strength of ions having mass-to-charge ratio (mass number of ion/valence of ion) values of 187 and 205, to detect 2-chlorovinyldichloroarsine.

22. A method for detecting chemical agents which comprises introducing a test sample, heating the test sample at 110° C. to 180° C., negatively ionizing the resulting gas by corona discharge, subjecting the resulting ions to mass spectrometry, and detecting signals due to a chemical agent to be detected.

23. An apparatus for detecting chemical agents according to claim 7, wherein a drift voltage applied between small-hole-provided electrodes provided on both sides of differential exhaust portion of the aforesaid mass spectrometry section is set at 50 V to 80 V.

24. An apparatus for detecting chemical agents according to claim 7, wherein the aforesaid chemical agent to be detected is 2,2'-dichloroethyl sulphide.

25. An apparatus for detecting chemical agents according to claim 23, wherein the aforesaid chemical agent to be detected is 2,2'-dichloroethyl sulphide.

26. An apparatus for detecting chemical agents according to claim 7, wherein the aforesaid monitoring means monitors the ionic strength of ions having mass-to-charge ratio (mass number of ion/valence of ion) values of 123 and 158 , to detect 2,2'-dichloroethyl sulphide.

27. An apparatus for detecting chemical agents according to claima 8; wherein the aforesaid monitoring means monitors the ionic strength of ions having mass-to-charge ratio (mass number of ion/valence of ion) of 123 and 158 , to detect 2, 2'-dichloroethyl sulphide.

28. An apparatus for detecting chemical agents according to claim 9, wherein the aforesaid monitoring means monitors the ionic strength of ions having mass-to-charge ratio (mass number of ion/valence of ion) values of 123 to 158 , to detect 2, 2'-dichloroethyl sulphide.

29. An apparatus for detecting chemical agents accordint to claim 18, wherein a drift voltage applied between small-hole-provided electrodes provided on both sides of the differential exhaust portion of the aforesaid mass spectrometry section is set −30 V to −60 V.

30. An apparatus for detecting chemical agents according to claim 18, wherein the aforesaid chemical agent to be detected is 2 -chlorovinyldichloroarsine.

31. An apparatus for detecting chemical agents according to claim 18, wherein the aforesaid monitoring means monitors the ionic strength of ions having mass-to-charge ratio (mass number of ion/valence of ion) values of 187 to 205 , to detect 2 -chlorovinyldichloroarsine.

32. An apparatus for detecting chemical agents according to claim 19, wherein the aforesaid monitoring means monitors the ionic strength of ions having mass-to-charge ratio (mass number of ion/valence of ion) values of 187 and 205 , to detect 2 -chlorovinyldichloroarsine.

33. An apparatus for detecting chemical agents according to claim 20, wherein the aforesaid monitoring means the ionic strength of ions having mass-to-charge ratio (mass number of ion/valence of ion) values of 187 and 205 , to detect 2 -chlorovinyldichloroarsine.

* * * * *

UNITED STATES PATENT AND TRADEMARK OFFICE
CERTIFICATE OF CORRECTION

PATENT NO. : 7,041,971 B2  Page 1 of 1
APPLICATION NO. : 10/644806
DATED : May 9, 2006
INVENTOR(S) : Fukano et al.

It is certified that error appears in the above-identified patent and that said Letters Patent is hereby corrected as shown below:

On Title page
Item (73) should read Assignees: Hitachi, Ltd., Tokyo (JP)
President of National Research Institute Of Police Science, Chiba (JP)

Signed and Sealed this

Twenty-third Day of January, 2007

JON W. DUDAS
*Director of the United States Patent and Trademark Office*